(12) United States Patent
Shuros et al.

(10) Patent No.: US 7,962,208 B2
(45) Date of Patent: Jun. 14, 2011

(54) METHOD AND APPARATUS FOR PACING DURING REVASCULARIZATION

(75) Inventors: Allan Shuros, St. Paul, MN (US); Tamara Colette Baynham, Blaine, MN (US); Jihong Qu, White Bear Lake, MN (US); Joseph M. Pastore, Woodbury, MN (US); Andrew P. Kramer, Stillwater, MN (US); Frits W. Prinzen, Maastricht (NL); Ward Y. R. Vanagt, Maastricht (NL); Richard N. Cornelussen, Maastricht (NL)

(73) Assignee: Cardiac Pacemakers, Inc., St. Paul, MN (US)

( * ) Notice: Subject to any disclaimer, the term of this patent is extended or adjusted under 35 U.S.C. 154(b) by 577 days.

(21) Appl. No.: 11/113,828

(22) Filed: Apr. 25, 2005

(65) Prior Publication Data

US 2006/0241704 A1    Oct. 26, 2006

(51) Int. Cl.
*A61N 1/08* (2006.01)

(52) U.S. Cl. ............................................ 607/9; 607/119

(58) Field of Classification Search .................. 607/1–3, 607/9, 119
See application file for complete search history.

(56) References Cited

U.S. PATENT DOCUMENTS

| | | | |
|---|---|---|---|
| 3,769,984 A | 11/1973 | Muench | |
| 3,837,347 A | 9/1974 | Tower | |
| 3,865,118 A | 2/1975 | Bures | |
| 3,893,461 A | 7/1975 | Preston | |
| 3,915,174 A | 10/1975 | Preston | |
| 3,942,536 A | 3/1976 | Mirowski et al. | |
| 3,949,757 A | 4/1976 | Sabel | |
| 4,030,508 A | 6/1977 | Thalen | |
| 4,094,321 A | 6/1978 | Muto | |
| 4,124,031 A | 11/1978 | Mensink et al. | |
| 4,136,702 A | 1/1979 | Trabucco | |
| 4,202,339 A | 5/1980 | Wirtzfeld et al. | |
| 4,262,982 A | 4/1981 | Kenny | |
| 4,365,639 A | 12/1982 | Goldreyer | |
| 4,388,930 A | 6/1983 | De Bellis | |
| 4,587,975 A * | 5/1986 | Salo et al. ..................... | 600/506 |
| 4,702,253 A | 10/1987 | Nappholz et al. | |
| 4,763,655 A | 8/1988 | Wirtzfeld et al. | |

(Continued)

FOREIGN PATENT DOCUMENTS

DE    3300050    7/1984

(Continued)

OTHER PUBLICATIONS

"Arrow Bipolar Pacing Catheters and Pacing Kits", *Arrow International*, (2000), 4 pgs.

(Continued)

*Primary Examiner* — Scott M Getzow
*Assistant Examiner* — Joseph M Dietrich
(74) *Attorney, Agent, or Firm* — Schwegman, Lundberg & Woessner, P.A.

(57) ABSTRACT

Cardiac protection pacing is applied to prevent or reduce cardiac injury and/or occurrences of arrhythmia associated with an ischemic event including the occlusion of a blood vessel during a revascularization procedure. Pacing pulses are generated from a pacemaker and delivered through one or more pacing electrodes incorporated onto a percutaneous transluminal vascular intervention (PTVI) device used in the revascularization procedure. The pacemaker generates the pacing pulses according to a predetermined cardiac protection pacing sequence before, during, and/or after the ischemic event.

21 Claims, 6 Drawing Sheets

U.S. PATENT DOCUMENTS

| | | |
|---|---|---|
| 4,809,697 A | 3/1989 | Causey, III et al. |
| 4,834,710 A | 5/1989 | Fleck |
| 4,882,777 A | 11/1989 | Narula |
| 4,919,133 A * | 4/1990 | Chiang .................. 606/159 |
| 4,955,382 A | 9/1990 | Franz et al. |
| 4,962,767 A | 10/1990 | Brownlee |
| 5,007,427 A | 4/1991 | Sukuki et al. |
| 5,025,786 A | 6/1991 | Siegel |
| 5,072,458 A | 12/1991 | Suzuki |
| 5,099,839 A | 3/1992 | Miyata et al. |
| 5,111,818 A | 5/1992 | Suzuki et al. |
| 5,121,750 A | 6/1992 | Katims |
| 5,127,403 A | 7/1992 | Brownlee |
| 5,131,406 A | 7/1992 | Kaltenbach |
| 5,143,089 A | 9/1992 | Alt |
| 5,154,169 A | 10/1992 | Miyata et al. |
| 5,154,387 A | 10/1992 | Trailer |
| 5,156,157 A | 10/1992 | Valenta, Jr. et al. |
| 5,170,802 A | 12/1992 | Mehra |
| 5,261,419 A | 11/1993 | Osypka |
| 5,285,781 A | 2/1994 | Brodard |
| 5,314,460 A | 5/1994 | Borghi |
| 5,336,251 A | 8/1994 | Borghi |
| 5,356,427 A | 10/1994 | Miyata et al. |
| 5,374,287 A | 12/1994 | Rubin |
| 5,387,232 A | 2/1995 | Trailer |
| 5,423,806 A | 6/1995 | Dale et al. |
| 5,466,255 A | 11/1995 | Franchi |
| 5,476,502 A | 12/1995 | Rubin |
| 5,483,022 A | 1/1996 | Mar |
| 5,484,419 A | 1/1996 | Fleck |
| 5,496,354 A | 3/1996 | DeBellis |
| 5,507,787 A | 4/1996 | Borghi |
| 5,531,779 A | 7/1996 | Dahl et al. |
| 5,545,191 A | 8/1996 | Mann et al. |
| 5,571,159 A | 11/1996 | Alt |
| 5,588,432 A * | 12/1996 | Crowley .................. 600/439 |
| 5,634,899 A * | 6/1997 | Shapland et al. ........... 607/120 |
| 5,674,217 A | 10/1997 | Wahlstrom et al. |
| 5,755,761 A | 5/1998 | Obino |
| 5,755,764 A | 5/1998 | Schroeppel |
| 5,760,341 A | 6/1998 | Laske et al. |
| 5,772,693 A | 6/1998 | Brownlee |
| 5,797,903 A | 8/1998 | Swanson et al. |
| 5,800,496 A | 9/1998 | Swoyer et al. |
| 5,814,076 A | 9/1998 | Brownlee |
| 5,843,132 A | 12/1998 | Ilvento |
| 5,851,206 A | 12/1998 | Guglielmi et al. |
| 5,906,207 A | 5/1999 | Shen |
| 5,921,935 A | 7/1999 | Hickey |
| 5,935,160 A | 8/1999 | Auricchio et al. |
| 5,954,761 A | 9/1999 | Macheck et al. |
| 5,997,536 A | 12/1999 | Osswald et al. |
| 6,014,579 A | 1/2000 | Pomeranz et al. |
| 6,023,638 A | 2/2000 | Swanson |
| 6,056,742 A | 5/2000 | Murphy-Chutorian et al. |
| 6,132,390 A | 10/2000 | Cookston et al. |
| 6,156,061 A | 12/2000 | Wallace et al. |
| 6,161,029 A | 12/2000 | Spreigl et al. |
| 6,167,315 A | 12/2000 | Coe et al. |
| 6,178,354 B1 | 1/2001 | Gibson |
| 6,183,469 B1 | 2/2001 | Thapliyal et al. |
| 6,238,390 B1 | 5/2001 | Tu et al. |
| 6,241,727 B1 | 6/2001 | Tu et al. |
| 6,272,379 B1 | 8/2001 | Fischell et al. |
| 6,324,434 B2 | 11/2001 | Coe et al. |
| 6,366,808 B1 | 4/2002 | Schroeppel et al. |
| 6,379,351 B1 | 4/2002 | Thapliyal et al. |
| 6,397,109 B1 | 5/2002 | Cammilli et al. |
| 6,451,016 B1 | 9/2002 | Karakozian |
| 6,477,402 B1 | 11/2002 | Lynch et al. |
| 6,477,427 B1 | 11/2002 | Stolz et al. |
| 6,501,983 B1 | 12/2002 | Natarajan et al. |
| 6,512,957 B1 | 1/2003 | Witte |
| 6,540,765 B2 | 4/2003 | Malacoff |
| 6,569,145 B1 | 5/2003 | Shmulewitz et al. |
| 6,584,362 B1 | 6/2003 | Scheiner et al. |
| 6,638,278 B2 | 10/2003 | Falwell et al. |
| 6,640,120 B1 | 10/2003 | Swanson |
| 6,690,970 B1 | 2/2004 | Taheri et al. |
| 6,697,676 B2 | 2/2004 | Dahl et al. |
| 6,709,390 B1 | 3/2004 | Marie Pop |
| 6,711,436 B1 | 3/2004 | Duhaylongsod |
| 6,711,440 B2 | 3/2004 | Deal et al. |
| 6,772,014 B2 | 8/2004 | Coe et al. |
| 6,813,516 B2 | 11/2004 | Ujhelyi et al. |
| 6,865,420 B1 | 3/2005 | Kroll |
| 6,909,920 B2 | 6/2005 | Lokhoff et al. |
| 6,950,701 B2 | 9/2005 | Begemann et al. |
| 6,980,858 B2 | 12/2005 | Fuimaono et al. |
| 6,988,001 B2 | 1/2006 | Greatbatch et al. |
| 6,999,809 B2 | 2/2006 | Currier et al. |
| 6,999,821 B2 | 2/2006 | Jenney et al. |
| 7,029,467 B2 | 4/2006 | Currier et al. |
| 7,295,874 B2 | 11/2007 | Prinzen et al. |
| 7,499,756 B2 | 3/2009 | Bowe et al. |
| 2002/0026228 A1 | 2/2002 | Schauerte |
| 2002/0042632 A1 | 4/2002 | Iaizzo et al. |
| 2002/0072777 A1 | 6/2002 | Lu |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2003/0004549 A1 | 1/2003 | Hill et al. |
| 2003/0009189 A1 * | 1/2003 | Gilson et al. .................. 606/200 |
| 2003/0045908 A1 | 3/2003 | Condie et al. |
| 2003/0060854 A1 | 3/2003 | Zhu |
| 2003/0109901 A1 | 6/2003 | Greatbatch |
| 2003/0125774 A1 | 7/2003 | Salo |
| 2003/0139778 A1 | 7/2003 | Fischell et al. |
| 2003/0158584 A1 | 8/2003 | Cates et al. |
| 2003/0204206 A1 | 10/2003 | Padua et al. |
| 2003/0204231 A1 | 10/2003 | Hine et al. |
| 2003/0229386 A1 | 12/2003 | Rosenman et al. |
| 2003/0233130 A1 | 12/2003 | Padmanabhan et al. |
| 2004/0010189 A1 | 1/2004 | van Sloun et al. |
| 2004/0015081 A1 * | 1/2004 | Kramer et al. .................. 607/9 |
| 2004/0038947 A1 | 2/2004 | Wink et al. |
| 2004/0088017 A1 | 5/2004 | Sharma et al. |
| 2004/0106960 A1 | 6/2004 | Siejko et al. |
| 2004/0116994 A1 | 6/2004 | De Bellis |
| 2004/0133247 A1 | 7/2004 | Stahmann et al. |
| 2004/0162599 A1 | 8/2004 | Kurth |
| 2004/0172081 A1 | 9/2004 | Wang |
| 2004/0214148 A1 | 10/2004 | Salvino et al. |
| 2004/0215139 A1 | 10/2004 | Cohen |
| 2004/0255956 A1 | 12/2004 | Vinten-Johansen et al. |
| 2005/0004476 A1 | 1/2005 | Payvar et al. |
| 2005/0038345 A1 | 2/2005 | Gorgenberg et al. |
| 2005/0075673 A1 | 4/2005 | Warkentin et al. |
| 2005/0137631 A1 | 6/2005 | Yu et al. |
| 2005/0137647 A1 | 6/2005 | Wallace et al. |
| 2005/0143780 A1 | 6/2005 | Henry et al. |
| 2005/0149155 A1 | 7/2005 | Scheiner et al. |
| 2005/0197674 A1 | 9/2005 | McCabe et al. |
| 2005/0222632 A1 | 10/2005 | Obino |
| 2005/0251239 A1 | 11/2005 | Wallace et al. |
| 2005/0288717 A1 | 12/2005 | Sunagawa |
| 2006/0009830 A1 | 1/2006 | Atkinson et al. |
| 2006/0036306 A1 | 2/2006 | Heist et al. |
| 2006/0058597 A1 | 3/2006 | Machado et al. |
| 2006/0100639 A1 | 5/2006 | Levin et al. |
| 2006/0100669 A1 | 5/2006 | Fuimaono et al. |
| 2006/0116593 A1 | 6/2006 | Zhang et al. |
| 2006/0136049 A1 * | 6/2006 | Rojo .................. 623/1.42 |
| 2006/0142660 A1 | 6/2006 | Maschke |
| 2006/0142812 A1 | 6/2006 | Ortega et al. |
| 2006/0149326 A1 | 7/2006 | Prinzen et al. |
| 2006/0178586 A1 | 8/2006 | Dobak |
| 2006/0184191 A1 | 8/2006 | O'Brien |
| 2006/0195038 A1 | 8/2006 | Carlson et al. |
| 2006/0241357 A1 | 10/2006 | Chirife |
| 2006/0241704 A1 | 10/2006 | Shuros et al. |
| 2006/0241733 A1 | 10/2006 | Zhang et al. |
| 2006/0241736 A1 | 10/2006 | Haldeman |
| 2006/0247700 A1 | 11/2006 | Jackson |
| 2006/0253156 A1 | 11/2006 | Pastore et al. |

| | | | |
|---|---|---|---|
| 2006/0259085 A1 | 11/2006 | Zhang et al. | |
| 2006/0259087 A1 | 11/2006 | Baynham et al. | |
| 2006/0259088 A1 | 11/2006 | Pastore et al. | |
| 2006/0287684 A1 | 12/2006 | Baynham et al. | |
| 2006/0293741 A1 | 12/2006 | Johnson et al. | |
| 2007/0021789 A1 | 1/2007 | Pastore et al. | |
| 2007/0054871 A1 | 3/2007 | Pastore et al. | |
| 2007/0055334 A1 | 3/2007 | Haldeman et al. | |
| 2007/0100410 A1 | 5/2007 | Lamson et al. | |
| 2007/0150005 A1 | 6/2007 | Sih et al. | |
| 2007/0150009 A1 | 6/2007 | Kveen et al. | |
| 2007/0233200 A1 | 10/2007 | Maschke | |
| 2008/0071315 A1 | 3/2008 | Baynham et al. | |
| 2008/0082136 A1 | 4/2008 | Gaudiani | |
| 2008/0114408 A1 | 5/2008 | Shuros et al. | |
| 2008/0288030 A1 | 11/2008 | Zhang et al. | |
| 2008/0319502 A1 | 12/2008 | Sunagawa et al. | |
| 2009/0005845 A1 | 1/2009 | David et al. | |
| 2009/0143835 A1 | 6/2009 | Pastore et al. | |
| 2009/0318943 A1 | 12/2009 | Eidenschink et al. | |
| 2009/0318984 A1 | 12/2009 | Mokelke et al. | |
| 2009/0318989 A1 | 12/2009 | Tomaschko et al. | |
| 2009/0318990 A1 | 12/2009 | Tomaschko et al. | |
| 2009/0318991 A1 | 12/2009 | Tomaschko et al. | |
| 2009/0318992 A1 | 12/2009 | Eidenschink et al. | |
| 2009/0318993 A1 | 12/2009 | Eidenschink et al. | |
| 2009/0318994 A1 | 12/2009 | Eidenschink et al. | |
| 2010/0056858 A1 | 3/2010 | Mokelke et al. | |
| 2010/0130913 A1 | 5/2010 | Baynham et al. | |

FOREIGN PATENT DOCUMENTS

| | | |
|---|---|---|
| EP | 1690566 A1 | 8/2006 |
| WO | WO-9518649 A1 | 7/1995 |
| WO | WO-0115609 A1 | 3/2001 |
| WO | WO-03035139 A1 | 5/2003 |
| WO | WO-2004058326 A1 | 7/2004 |
| WO | WO-2004058326 A2 | 7/2004 |
| WO | WO-2005065771 A1 | 7/2005 |
| WO | WO-2006115693 A2 | 11/2006 |
| WO | WO-2006115693 A3 | 11/2006 |
| WO | WO-2006124636 A2 | 11/2006 |
| WO | WO-2006124636 A3 | 11/2006 |
| WO | WO-2006124729 A2 | 11/2006 |
| WO | WO-2006124729 A3 | 11/2006 |
| WO | WO-2007133962 A2 | 11/2007 |
| WO | WO-2007133962 A3 | 11/2007 |
| WO | WO-2008027261 A1 | 3/2008 |
| WO | WO-2009154720 A1 | 12/2009 |

OTHER PUBLICATIONS

"Coronary Dilatation Catheters", http://www.guidant.com/products/TemplatePDFs/NoPriceDilataticatheters.pdf, (2005),3 pgs.

"Guidant Product Catalog", http://www.guidant.com/products/VIproductcataloq.pdf, (Jan. 6, 2005),133 pgs.

"Product Overview: RX ACCULINK Carotid Stent System; RX ACCUNET Embolic Protection System", http://www.guidant.com/webapp/emarketing/ppt/acculink/ACCULINK.pdf, (2005),22 pgs.

"RX ACCUNET Embolic Protection System", http://www.guidant.com/products/ProductTemplates/ES/accunet.shtml, (2005),4 pgs.

"RX ACCUNET Embolic Protection System: Information for Prescribers", http://www.guidant.com/products/TemplatePDFs/AC-CUNET_RX.pdf, (Jan. 6, 2005),32 pgs.

"VOYAGER RX Coronary Dilatation Catheter", http://www.guidant.com/products/ProductTemplates/VI/RX_US_Voyager_Intro.shtml, (2005),2 pgs.

Airaksinen, K. E., et al., "Antiarrhythmic effect of repeated coronary occlusion during balloon angioplasty", *J Am Coll Cardiol.*, 29(5), (Apr. 1997),1035-1038.

Girouard, Steven D., "Pulmonary Vein Stent for Treating Atrial Fibrillation", U.S. Appl. No. 60/298,741, filed Jun. 15, 2001, 14 pgs.

Henriques, Jose P., et al., "Outcome of primary angioplasty for acute myocardial infarction during routine duty hours versus during off-hours", *J Am Coll Cardiol*, 41(12), (Jun. 18, 2003),2138-42.

Kin, Hajime , et al., "Postconditioning attenuates myocardial ischemia-reperfusion injury by inhibiting events in the early minutes of reperfusion", *Cardiovascular Research*, 62(1), (Apr. 1, 2004),74-85.

Koning, M M., et al., "Rapid ventricular pacing produces myocardial protection by nonischemic activation of KATP+ channels", *Circulation*, 93(1), (Jan. 1, 1996),179-86.

Tsang, A. , "Postconditioning: a form of "modified reperfusion" protects the myocardium by activating the phosphatidylinositol 3-kinase-Akt pathway.", *Circ Res.*, 95(3), Epub Jul. 8, 2004, (Aug. 6, 2004),230-2.

Vanagt, Ward Y.R., et al., "Ventricular Pacing for Improving Myocardial Tolerance to Ischemia, Progress Report on Project Guidant-CARIM", (Oct. 2003).

Vegh, A , et al., "Transient ischaemia induced by rapid cardiac pacing results in myocardial preconditioning", *Cardiovascular Research*, 25(12), (Dec. 1991),1051-3.

Wu, Zhong-Kai , et al., "Ischemic preconditioning suppresses ventricular tachyarrhythmias after myocardial revascularization", *Circulation*, 106(24), (Dec. 10, 2002),3091-3096.

Yang, S. M., et al., "Multiple, brief coronary occlusions during early reperfusion protect rabbit hearts by targeting cell signaling pathways", *Journal of the American College of Cardiology*, 44(5), (Sep. 1, 2004),1103-1110.

Zhao, Zhi-Qing , et al., "Inhibition of myocardial injury by ischemic postconditioning during reperfusion: comparison with ischemic preconditioning", *Am J Physiol Heart Circ Physiol*, 285(2), (Aug. 2003),H579-H588.

"U.S. Appl. No. 11/030,575 Non Final Office Action mailed Jul. 26, 2006", 11 pgs.

"U.S. Appl. No. 11/030,575 Response filed Oct. 26, 2006 to Non Final Office Action mailed Jul. 26, 2006", 8 pgs.

"U.S. Appl. No. 11/129,050, Non-Final Office Action mailed Nov. 26, 2007", OARN,14 pgs.

"U.S. Appl. No. 11/129,050, Response filed Sep. 28, 2007 to Restriction Requirement mailed Aug. 1, 2007", 11 pgs.

"U.S. Appl. No. 11/129,058 Final Office Action Received Jul. 9, 2007", 17 pgs.

"U.S. Appl. No. 11/129,058 Non Final office action mailed Jan. 29, 2007", 12 pgs.

"U.S. Appl. No. 11/129,058 Response filed Apr. 30, 2007 to Non Final office action mailed Jan. 29, 2007", 16 pgs.

"U.S. Appl. No. 11/129,058, Response filed Oct. 9, 2007 to Final Office Action mailed Jul. 9, 2007", 14 pgs.

"International Search Report and Written Opinion for Application No. PCT/US2006/018642, Date mailed Oct. 24, 2006", 14 Pages.

Brockway, Marina V., et al., "Method and Apparatus for Delivering Chronic and Post-Ischemia Cardiac Therapies", U.S. Appl. No. 11/207,251, filed Aug. 19, 2005, 40 Pages.

Murry, C. E., "Preconditioning with ischemia: a delay of lethal cell injury in ischemic myocardium", *Circulation*, 74(5), (1986),1124-1136.

Ovize, M. , et al., "Stretch preconditions canine myocardium.", *Am J Physiol.*, 266(1 Pt 2), (Jan. 1994),H137-46.

"International Search Report and Written Opinion for Application No. PCT/US2006/011972", 16 Pages.

Baynham, Tamara C., et al., "Integrated Catheter and Pulse Generator Systems and Methods", U.S. Appl. No. 11/468,875, filed Aug. 31, 2006, 23 Pages.

Baynham, Tamara C., et al., "Method and Apparatus for Initiating and Delivering Cardiac Protection Pacing", U.S. Appl. No. 11/382,849, filed May 11, 2006, 37 Pages.

Kis, A., "Repeated cardiac pacing extends the time during which canine hearts are protected against ischaemia-induced arrhythmias : role of nitric oxide.", *Journal of Molecular and Cellular Cardiology*, 31(6), (Jun. 1999),1229-1241.

Meier, B., et al., "Coronary Pacing During Percutaneous Transluminal Coronary Angioplasty", *Therapy And Prevention Cardiac Pacing*, 71(3), (Mar. 1985),557-561.

Pastore, Joseph M., et al., "Intermittent Stress Augmentation Pacing for Cardioprotective Effect", U.S. Appl. No. 11/458,286, filed Jul. 18, 2006, 23 Pages.

"U.S. Appl. No. 11/129,050, Response filed Feb. 26, 2008 to Non-Final Office Action mailed Nov. 26, 2007", 14 pgs.

"U.S. Appl. No. 11/129,050 Final Office Action mailed May 12, 2008", 9 pgs.

"PCT Application No. PCT/US2007/018577, International Search Report mailed Jan. 15, 2008", 4 pgs.

"PCT Application No. PCT/US2007/018577, Written Opinion mailed Jan. 15, 2008", 7 pgs.

"PCT Application No. PCT/US2007/068217, International Search Report mailed Oct. 30, 2007", 5 pgs.

"PCT Application No. PCT/US2007/068217, Written Opinion mailed Oct. 30, 2007", 8 pgs.

Rosa, A., et al., "Ectopic Pacing at Physiological Rate Improves Postanoxic Recovery of the Developing Heart", *Am. J. Physiol.— Heart Circ. Physiol.*, 284, (2003),H2384-H2392.

"U.S. Appl. No. 11/129,050, Response filed Jul. 14, 2008 to Final Office Action mailed May 12, 2008", 13 pgs.

"U.S. Appl. No. 11/129,050, Supplemental Amendment and Response filed Sep. 12, 2008 to Final Office Action mailed May 12, 2008 and the Advisory Action mailed Jul. 28, 2008", 12 pgs.

"U.S. Appl. No. 11/129,050 Non-Final Office Action mailed Nov. 6, 2008", 9 pgs.

"U.S. Appl. No. 11/129,058, Advisory Action mailed Oct. 17, 2007", 3 pgs.

"U.S. Appl. No. 11/129,058, Appeal Brief filed Jan. 8, 2008", 22 pgs.

"U.S. Appl. No. 11/129,058, Examiner's Answer mailed Jun. 18, 2008", 14 pgs.

Heinroth, K. M, et al., "Temporary transcoronary pacing by coated guidewires", *Clin Res Cardiol.*, 95, (2006), 1-6.

"U.S. Appl. No. 11/129,050, Response filed Feb. 23, 2009 to Non Final Office Action mailed Nov. 6, 2008", 13 pgs.

"U.S. Appl. No. 11/468,875, Response filed Mar. 9, 2009 to Non Final Office Action mailed Dec. 11, 2008", 10 pgs.

"U.S. Appl. No. 11/468,875 Non-Final Office Action mailed Dec. 11, 2008.", 9 pgs.

"U.S. Appl. No. 11/113,828, Non-Final Office Action mailed Mar. 5, 2008", 8 pgs, 9 pgs.

07797336.0, "European Application Serial No. 07797336.0, Office Action mailed Feb. 24, 2009", 4 pgs.

"U.S. Appl. No. 11/382,849, Non-Final Office Action mailed Aug. 31, 2009", 8 pgs.

"U.S. Appl. No. 11/129,050, Advisory Action mailed Jul. 14, 2009", 3 pgs.

"U.S. Appl. No. 11/129,050, Final Office Action mailed Apr. 21, 2009", 10 pgs.

"U.S. Appl. No. 11/129,050, Notice of Allowance mailed Aug. 24, 2009", 7 pgs.

"U.S. Appl. No. 11/129,050, Response filed Jun. 22, 2009 to Final Office Action mailed Apr. 21, 2009", 9 pgs.

"U.S. Appl. No. 11/382,489, Restriction Requirement mailed May 6, 2009", 6 pgs.

"U.S. Appl. No. 11/382,489, Response filed Jun. 8, 2009 to Restriction Requirement mailed May 6, 2009", 8 pgs.

"U.S. Appl. No. 11/468,875, Advisory Action mailed Aug. 19, 2009", 3 pgs.

"U.S. Appl. No. 11/468,875, Final Office Action mailed Jun. 1, 2009", 6 pgs.

"U.S. Appl. No. 11/468,875, Response filed Aug. 3, 2009 to Final Office Action mailed Jun. 1, 2009", 8 pgs.

"U.S. Appl. No. 11/468,875, Amendment and Response filed Sep. 1, 2009 to Advisory Action mailed Aug. 19, 2009 and the Final Office Action mailed Jun. 1, 2009", 9 pgs.

"International Application Serial No. PCT/US/2009/003589, International Search Report mailed Sep. 14, 2009", 5 pgs.

"International Application Serial No. PCT/US/2009/003589, Written Opinion mailed Sep. 14, 2009", 11 pgs.

"International Application Serial No. PCT/US2009/003575, International Search Report mailed Sep. 14, 2009", 6 pgs.

"International Application Serial No. PCT/US2009/003575, Written Opinion mailed Sep. 14, 2009", 9 pgs.

"International Application Serial No. PCT/US2009/003577, International Search Report mailed Aug. 9, 2009", 5 pgs.

"International Application Serial No. PCT/US2009/003577, Written Opinion mailed Aug. 9, 2009", 10 pgs.

"International Application Serial No. PCT/US2009/003581, International Search Report mailed Sep. 21, 2009", 5 pgs.

"International Application Serial No. PCT/US2009/003581, Written Opinion mailed Sep. 21, 2009", 10 pgs.

"International Application Serial No. PCT/US2009/003590, International Search Report mailed Sep. 14, 2009", 5 pgs.

"International Application Serial No. PCT/US2009/003590, Written Opinion mailed Sep. 14, 2009", 10 pgs.

"International Application Serial No. PCT/US2009/003594, International Search Report mailed Sep. 17, 2009", 5 pgs.

"International Application Serial No. PCT/US2009/003594, Written Opinion mailed Sep. 17, 2009", 9 pgs.

"U.S. Appl. No. 11/129,050, Notice of Allowance mailed Dec. 2, 2009", 4 pgs.

"U.S. Appl. No. 11/129,058, Decision on Appeal mailed Nov. 4, 2009", 15 pgs.

"U.S. Appl. No. 11/382,849 Final Office Action mailed Jan. 28, 2010", 8 pgs.

"U.S. Appl. No. 11/382,849, Response filed Nov. 30, 2009 to Non Final Office Action mailed Aug. 31, 2009", 11 pgs.

"European Application Serial No. 06740227.1, Communication dated Dec. 27, 2007", 2 pgs.

"European Application Serial No. 06740227.1, Response filed Jan. 27, 2008 to Communication dated Dec. 27, 2007", 9 pgs.

"European Application Serial No. 06752540.2, Communication Mar. 3, 2008", 2 pgs.

"European Application Serial No. 06752540.2, Response filed Apr. 9, 2008 to Communication Mar. 3, 2008", 6 pgs.

"European Application Serial No. 06762527.9, Communication pursuant to Rules 161 to 182 EPC mailed Mar. 3, 2008", 2 pgs.

"European Application Serial No. 06762527.9, Response filed Apr. 9, 2008 to Communication pursuant to Rules 161 to 182 EPC mailed Mar. 3, 2008", 6 pgs.

"European Application Serial No. 07837205.9, Communication dated Apr. 8, 2009", 2 pgs.

"International Application Serial No. PCT/US2006/018497, International Search Report mailed Oct. 24, 2006", 5 pgs.

"International Application Serial No. PCT/US2006/018497, Written Opinion mailed Oct. 24, 2006", 7 pgs.

"U.S. Appl. No. 11/129,050 Notice of Allowance mailed Jul. 16, 2010", 4 pgs.

"U.S. Appl. No. 11/129,050, Interview Summary mailed Feb. 11, 2009", 2 pgs.

"U.S. Appl. No. 11/129,050, Notice of Allowance mailed Apr. 1, 2010", 6 pgs.

"U.S. Appl. No. 11/129,058, Office Communication mailed Jan. 15, 2010", 2 pgs.

"U.S. Appl. No. 11/382,849, Non-Final Office Action mailed May 12, 2010", 5 pgs.

"U.S. Appl. No. 11/382,849, Response filed Apr. 26, 2010 to Final Office Action mailed Jan. 28, 2010", 10 pgs.

"U.S. Appl. No. 11/382,849, Response filed Aug. 2, 2010 to Non Final Office Action mailed May 12, 2010", 7 pgs.

"U.S. Appl. No. 11/868,767, Notice of Allowance mailed Sep. 17, 2010", 5 pgs.

"U.S. Appl. No. 11/868,767, Notice of Allowance mailed Mar. 24, 2010", 7 pgs.

"Australian Application Serial No. 2007290672, First Examiner Report Received mailed Aug. 23, 2010", 2 pgs.

"European Application Serial No. 06752527.9, Communication mailed Mar. 8, 2010", 6 pgs.

"European Application Serial No. 06752527.9, Response mailed Jul. 7, 2010 to Communication mailed Mar. 8, 2010", 15 pgs.

"European Application Serial No. 06752527.9, Summons to Attend Oral Proceedings Received mailed Jul. 23, 2010", 3 pgs.

"European Application Serial No. 06752540.2, Communication mailed Mar. 8, 2010", 2 pgs.

"European Application Serial No. 06752540.2, Response filed Jul. 15, 2010 to Communication mailed Mar. 8, 2010", 20 pgs.

"European Application Serial No. 07797336.0, Communication mailed Mar. 10, 2010", 3 pgs.

"European Application Serial No. 07797336.0, Response filed Jul. 7, 2010" to Communication mailed Mar. 10, 2010, 5 pgs.

"European Application Serial No. 07797336.0, Response filed Jul. 6, 2009 to Communication mailed Feb. 24, 2009", 20 pgs.

"International Application Serial No. PCT/US2006/018642, International Search Report mailed Oct. 24, 2006", 5 pgs.

"International Application Serial No. PCT/US2006/018642, Written Opinion mailed Oct. 24, 2006", 7 pgs.

"Japanese Application Serial No. 2008-511421, Voluntary Amendment filed Apr. 27, 2009", (w/ English Translation of Amended Claims), 11 pgs.

"Japanese Application Serial No. 2008-511452, Voluntary Amendment filed May 11, 2009", (w/ English Translation of Amended Claims), 8 pgs.

"Japanese Application Serial No. 2009-510093, Voluntary Amendment filed Jan. 14, 2009", 4 pgs.

"U.S. Appl. No. 11/129,050, Examiner Interview Summary mailed Feb. 11, 2009", 2 pgs.

"U.S. Appl. No. 11/129,050, Notice of Allowance mailed Jul. 16, 2010", 4 pgs.

"European Application Serial No. 06752527.9, Office Action Response mailed Jul. 7, 2010", 15 pgs.

"European Application Serial No. 07797336.0, Response Filed Jul. 7, 2010 to Office Action dated Mar. 10, 2010", 5 pgs.

* cited by examiner

METHOD AND APPARATUS FOR PACING DURING REVASCULARIZATION

TECHNICAL FIELD

This document relates generally to cardiac pacing systems and particularly to a system for delivering pacing pulses during a revascularization procedure.

BACKGROUND

The heart is the center of a person's circulatory system. It includes an electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the body organs and pump it to the lungs where the blood gets oxygenated. These pumping functions are resulted from contractions of the myocardium (cardiac muscles). In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition where the heart fails to pump enough blood to meet the body's metabolic needs is known as heart failure.

Myocardial infarction (MI) is the necrosis of portions of the myocardial tissue resulted from cardiac ischemia, a condition in which the myocardium is deprived of adequate oxygen and metabolite removal due to an interruption in blood supply caused by an occlusion of a blood vessel such as a coronary artery. The necrotic tissue, known as infarcted tissue, loses the contractile properties of the normal, healthy myocardial tissue. Consequently, the overall contractility of the myocardium is weakened, resulting in an impaired hemodynamic performance. Following an MI, cardiac remodeling starts with expansion of the region of infarcted tissue and progresses to a chronic, global expansion in the size and change in the shape of the entire left ventricle. The consequences include a further impaired hemodynamic performance and a significantly increased risk of developing heart failure.

When a blood vessel such as the coronary artery is partially or completely occluded, a revascularization procedure such as percutaneous transluminal coronary angioplasty (PCTA) can be performed to reopen the occluded blood vessel. However, the revascularization procedure itself involves a temporary occlusion of the coronary artery. In addition, plaques dislodged and displaced by the revascularization procedure may enter small blood vessels branching from the blood vessel in which the revascularization is performed, causing occlusion of these small blood vessels. This complication is referred to as "snow plow effect." The revascularization procedure may also cause distal embolization, i.e., obstruction of the artery caused by the plaque dislodged during the procedure. The temporary occlusion, snow plow effect, and distal embolization may each cause cardiac injuries such as further expansion of the region of infarcted tissue. In addition, the revascularization procedure is known to increase the risk for occurrences of arrhythmia.

Therefore, there is a need for minimizing cardiac injury and preventing arrhythmias during the revascularization procedure.

SUMMARY

Cardiac protection pacing is applied to prevent or reduce cardiac injury and/or occurrences of arrhythmia associated with an ischemic event including the occlusion of a blood vessel during a revascularization procedure. Pacing pulses are generated from a pacemaker and delivered through one or more pacing electrodes incorporated onto a percutaneous transluminal vascular intervention (PTVI) device used in the revascularization procedure. The pacemaker generates the pacing pulses according to predetermined cardiac protection pacing sequence before, during, and/or after the schemic event.

In one embodiment, a pacemaker includes a pacing output circuit and a control circuit. The control circuit includes a cardiac protection pacing sequence timer that times a predetermined cardiac protection pacing sequence. The predetermined cardiac protection pacing sequence includes alternating pacing and non-pacing periods. The pacing periods each have a predetermined pacing duration during which a plurality of pacing pulses are delivered from the pacing output circuit in a predetermined pacing mode. The non-pacing periods each have a predetermined non-pacing duration during which no pacing pulse is delivered.

In one embodiment, a PTVI device includes a proximal end portion, a distal end portion, and an elongate body. The proximal end portion includes one or more connectors for connecting to a pacemaker. The distal end portion is configured for intravascular placement. The elongate body is coupled between the proximal end portion and the distal end portion. One or more pacing electrodes are incorporated onto the distal end portion. One or more conductors within the elongate body each connect one of the one or more pacing electrodes to one of the one or more connectors. In a further embodiment, the distal end portion includes a tip and an angioplasty device. The angioplasty device has one end approximately adjacent to the tip and another end coupled to the elongate body.

In one embodiment, a method for operating a system providing for cardiac protection pacing is provided. A predetermined pacing sequence is timed. The predetermined pacing sequence includes alternating pacing and non-pacing periods. The pacing periods each have a predetermined pacing duration during which a plurality of pacing pulses are delivered in a predetermined pacing mode. The plurality of pacing pulses are delivered to one or more pacing electrodes incorporated onto a PTVI device.

In one embodiment, a method for making a PTVI device is provided. The PTVI device has a distal end portion configured for intravascular placement. One or more pacing electrodes are incorporated onto that distal end portion.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof.

The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a pacing system for minimizing damage to the myocardial tissue and preventing arrhythmias during a revascularization procedure that requires temporary occlusion of one or more blood vessels. In a specific application, this system provides for cardiac protection pacing during a percutaneous transluminal coronary angioplasty (PTCA) procedure. Cardiac protection pacing includes the delivery of a pacing therapy before, during, and/or after the temporary occlusion of a coronary artery associated with the PTCA procedure, for preventing or reducing adverse effects of the occlusion, which is an ischemic event. The pacing therapy can be delivered at almost any time during a revascularization procedure, as soon as pacing electrodes are in place, without substantially interfering with the revascularization procedure.

To deliver pacing pulses during a revascularization procedure, one or more pacing electrodes are incorporated onto the distal end portion of a PTVI device. Examples of such PTVI device include guide wires, dilatation balloon catheters, stent delivery systems, brachytherapy devices, atherectomy devices, distal embolization protection devices, and guiding catheters. A pacemaker is connected to the proximal end portion of the PTVI device to deliver the pacing pulses to the heart through the one or more electrodes. In one embodiment, the pacemaker is an external pacing device such as a pacing system analyzer. This approach to cardiac protection pacing allows delivery of pacing pulses as soon as the PTVI device is inserted.

Figure 1:
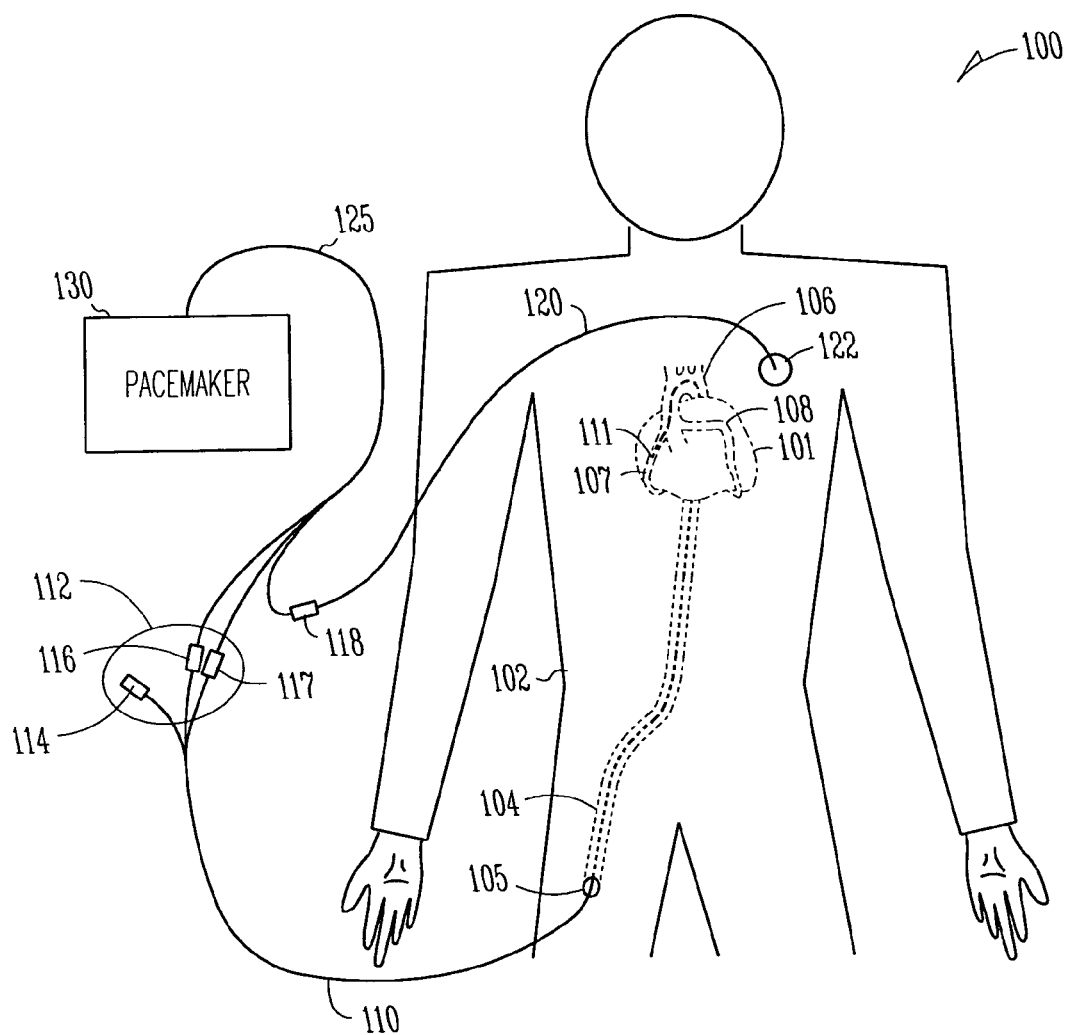
FIG. 1 is an illustration of an embodiment of a system providing for pacing during revascularization and portions of an environment in which the system is used.

FIG. 1 is an illustration of an embodiment of a system 100 providing for pacing during revascularization and portions of an environment in which system 100 is used. System 100 includes a PTVI device 110, a pacemaker 130, and a cable 125 connecting PTVI device 110 and pacemaker 130. When needed, system 100 also includes a reference electrode 122, which is a surface electrode, such as a skin patch electrode, connected to a lead 120. Lead 120 is connected to a connector 118 allowing its connection to cable 125.

PTVI device 110 is used during a revascularization procedure and includes a distal end portion 111 for intravascular placement and a proximal end portion 112. Proximal end portion 112 includes a proximal end device 114 and pacing connectors 116 and 117. Proximal end device 114 includes various connectors and other structures allowing manipulation of PTVI device 110 including the percutaneous transluminal insertion of the device and operation of an angioplasty device at distal end 111. Pacing connectors 116 and 117 provide for electrical connections between cable 125 and PTVI device 110. In one embodiment, as illustrated in FIG. 1, PTVI device 110 is a percutaneous transluminal coronary angioplasty (PTCA) device used in a PTCA procedure. During the PTCA procedure, an opening 105 is made on a femoral artery 104 in a patient's body 102. PTVI device 110 is inserted into femoral artery 104 and advanced to an aorta 106 and then to a right coronary artery 107, which is narrowed or blocked. The angioplasty device at distal end 111 is then used to open up the blocked right coronary artery 107. In another embodiment, PTVI device 110 is used to open up a blocked left coronary artery 108.

Distal end portion 111 of PTVI device 110 includes one or more pacing electrodes to allow pacing pulses to be delivered to a heart 101 during the PTCA procedure. In one embodiment, pacing pulses are delivered through two pacing electrodes on distal end portion 111 of PTVI device 110. In another embodiment, pacing pulses are delivered through a pacing electrode on distal end portion 111 of PTVI device 110 and surface electrode 122 functioning as the return electrode for pacing.

Pacemaker 130 delivers pacing pulses by following a cardiac protection pacing sequence. In one embodiment, the cardiac protection pacing sequence provides for cardiac protection pacing following an ischemic event to prevent arrhythmias and cardiac injuries caused by the ischemic event. In one embodiment, pacemaker 130 is an external pacemaker such as a pacing system analyzer (PSA). In another embodiment, pacemaker 130 includes an implantable pacemaker adapted for external use.

It is to be understood that FIG. 1 is for illustrative, but not restrictive, purposes. For example, the physical structure of proximal end portion 112 depends on functional and ease-of-use considerations. Proximal end device 114 represents a structure that accommodates all the mechanical connection and access requirements, which depend on the specific configuration and function of PTVI device 110. In one embodiment, proximal end device 114 includes an integrated device as illustrated in FIG. 1. In another embodiment, proximal end device 114 branches out into multiple connectors and/or other devices. Pacing connectors 116 and 117 represent a structure that accommodates all the electrical connections required for delivering pacing pulses from pacemaker 130 to PTVI device 110. The number of pacing connectors depends on the number of pacing electrodes incorporated onto PTVI device 110 and how it is to be connected to cable 125. In one embodiment, when more than one electrical connection is incorporated onto PTVI device 110, proximal end portion 112 includes ranched-out pacing connectors such as pacing connectors 116 and 117 as illustrated in FIG. 1. In another embodiment, proximal end portion 112 includes a single connector providing for multiple, independent electrical connections.

Figure 2:
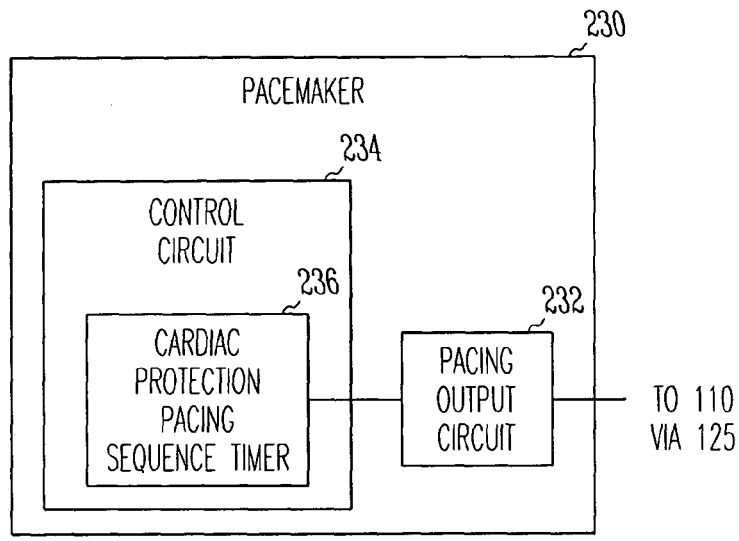
FIG. 2 is an illustration of an embodiment of a pacemaker providing for pacing during revascularization.

FIG. 2 is an illustration of an embodiment of a pacemaker 230 that provides for pacing during revascularization. Pacemaker 230 is a specific embodiment of pacemaker 130 and includes a pacing output circuit 232 and a control circuit 234. In one embodiment, pacemaker 230 further includes a user interface to allow a user to control the delivery of the pacing pulses by controlling the pacing parameters and/or the timing of the delivery.

Pacing output circuit 232 delivers pacing pulses to PTVI device 110 through cable 125. Control circuit 234 controls the delivery of the pacing pulses. In one embodiment, as illustrated in FIG. 2, control circuit 234 includes a cardiac protection pacing sequence timer 236, which times a predetermined cardiac protection pacing sequence. The cardiac protection pacing sequence is predetermined to provide cardiac protection pacing before, during, and/or after an ischemic event such as the occlusion of a coronary artery by PTVI device 110 during a PTCA procedure.

Figure 3:
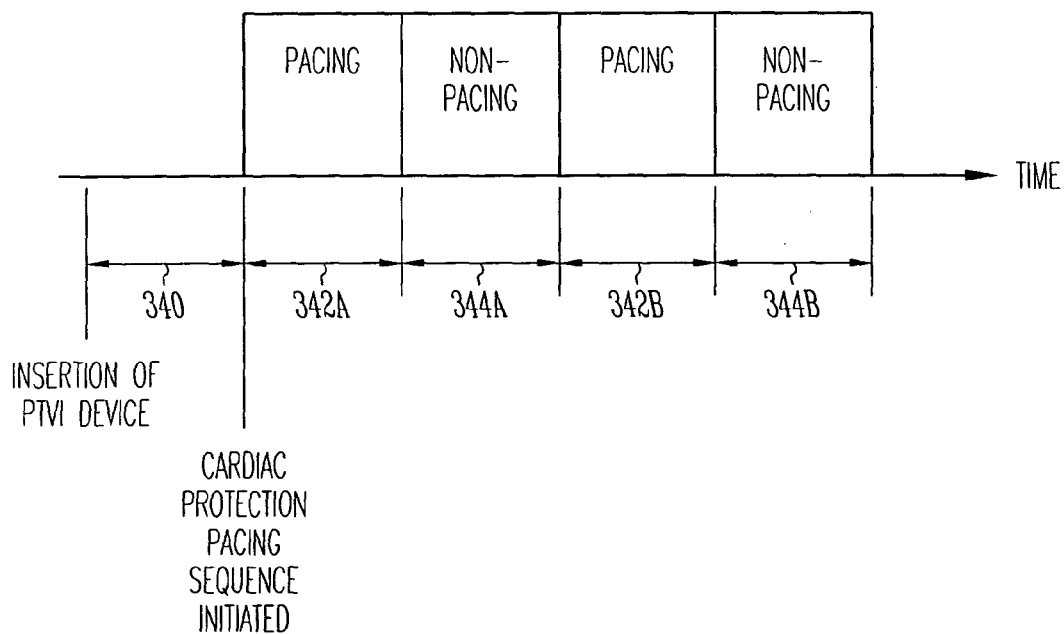
FIG. 3 is a timing diagram illustrating an exemplary embodiment of a cardiac protection pacing sequence for the pacing during revascularization.

FIG. 3 is a timing diagram illustrating an exemplary embodiment of a cardiac protection pacing sequence for pacing during a revascularization procedure such as a PTCA procedure. The cardiac protection pacing sequence is initiated after a time interval 340, which starts when the insertion of PTVI device into body 102 is completed. Time interval 340 expires before, during, and/or after an ischemic event that occurs when the blood vessel at the revascularization site is substantially occluded by PTVI device 110. In one embodiment, the cardiac protection pacing sequence is applied repeatedly, before, during, and/or after the ischemic event, during the revascularization procedure.

In the embodiment illustrated in FIG. 3, the cardiac protection pacing sequence includes alternating pacing and non-pacing periods. Each pacing period is a pacing duration during which the pacing pulses are delivered in a predetermined pacing mode. The non-pacing period is a non-pacing duration during which no pacing pulses is delivered. In one embodiment, during each pacing period, rapid, asynchronous pacing is applied. In other words, pacing pulses are delivered at a rate substantially higher than the patient's intrinsic heart rate without being synchronized to the patient's intrinsic cardiac contractions. For illustrative purpose only, FIG. 3 shows a cardiac protection pacing sequence that includes two cycles of alternating pacing and non-pacing periods: pacing period 342A, non-pacing periods 344A, pacing period 342B, and non-pacing periods 344B. In one embodiment, the number of the cycles of alternating pacing and non-pacing periods is programmable, and each of the pacing and non-pacing periods is programmable. In one embodiment, the cardiac protection pacing sequence is initiated before the ischemic event and includes approximately 1 to 4 cycles of alternating pacing and non-pacing periods. The pacing period is in a range of approximately 30 seconds to 20 minutes. The non-pacing period is in a range of approximately 30 seconds to 20 minutes. In a specific example, the cardiac protection pacing sequence initiated before the ischemic event includes 3 cycles of alternating pacing and non-pacing periods each being approximately 5-minute long. In one embodiment, the cardiac protection pacing sequence is initiated during the ischemic event and includes approximately 1 to 4 cycles of alternating pacing and non-pacing periods. The pacing period is in a range of approximately 30 seconds to 20 minutes. The non-pacing period is in a range of approximately 30 seconds to 20 minutes. In a specific example, the cardiac protection pacing sequence delivered during the ischemic event includes 3 cycles of alternating pacing and non-pacing periods each being approximately 5-minute long. In one embodiment, the cardiac protection pacing sequence is initiated after the ischemic event and includes approximately 1 to 4 cycles of alternating pacing and non-pacing periods. The pacing period is in a range of approximately 10 seconds to one minute. The non-pacing period is in a range of approximately 10 seconds to one minute. In one specific example, the cardiac protection pacing sequence delivered after the ischemic event includes 2 to 4 cycles of alternating pacing and non-pacing periods each being approximately 30-second long.

In various other embodiments, the cardiac protection pacing sequence includes pacing at one or more atrial tracking or other pacing modes. Examples of pacing modes used in such a cardiac protection pacing sequence include VDD, VVI, and DDD modes. In various embodiments, the VVI and DDD modes are delivered with a lower rate limit higher than the patient's intrinsic heart rate. In one embodiment, pacing therapy is delivered to prevent restenosis. In another embodiment, pacing therapy is delivered to treat an arrhythmia during the revascularization procedure, for example, when the patient experiences bradycardia during the procedure.

In one embodiment, the pacing pulses are delivered according to the cardiac protection pacing sequence through PTVI device 110 during the revascularization procedure. After the revascularization procedure, if an implantable pacemaker is implanted into the patient, pacing therapy is delivered to heart 101 through one or more implantable leads from the implantable pacemaker. The pacing therapy includes delivering pacing pulses according to a pacing sequence that is substantially identical or similar to the cardiac protection pacing sequence applied during the revascularization procedure. The pacing sequence is delivered according to a predetermined schedule, such as on a predetermined periodic basis. This prevents or reduces possible cardiac injury after the revascularization, including cardiac injury and occurrences of arrhythmia caused by ischemic events including myocardial infarction that may be experienced by the patient after the implantation of the implantable pacemaker.

Figure 4:
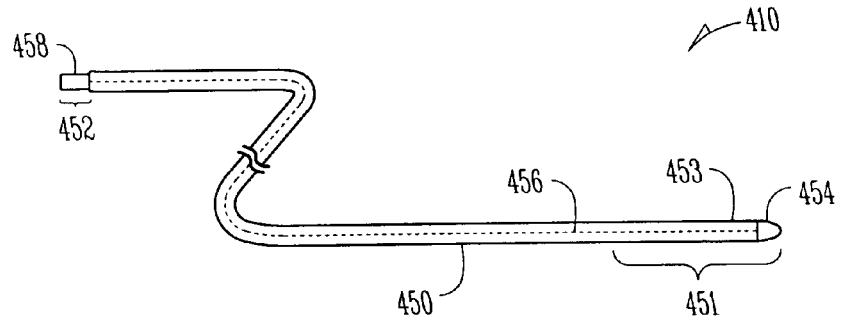
FIG. 4 is an illustration of an embodiment of a PTVI device with pacing electrodes.

FIG. 4 is an illustration of an embodiment of a PTVI device 410. PTVI device 410 is a specific embodiment of PTVI device 110 and has an elongate body 450 between a distal end portion 451 and a proximal end portion 452. Distal end portion 451 is configured for intravascular placement and includes a distal tip 453. Distal tip 453 includes a pacing electrode 454. A conductor 456 extends longitudinally within elongate body 450 and connected between pacing electrode 454 and a connector 458, which is part of proximal end portion 452.

In one embodiment, elongate body 450 is an elongate cylindrical shaft having a diameter in a range of approximately 0.2 mm to 1.5 mm, and PTVI device 410 has a length in a range of approximately 30 cm to 300 cm. In another embodiment, elongate body 450 is an elongate tubular body having an outer diameter in a range of approximately 0.5 mm to 8 mm and an inner diameter (of a lumen) in a range of approximately 0.4 mm to 7 mm. In one embodiment, PTVI device 410 is a guide wire such as a coronary guide wire. PTVI device 410 is formed by conductor 456, which is insulated throughout its length except for pacing electrode 454 and connector 458. As the core of the guide wire, conductor 456 is made of a metallic material such as stainless steel, alloys of nickel, titanium, and cobalt, and is insulated with a material such as silicone, polyurethane, Teflon, and polytetrafluoroethylene (PTFE). Electrode 454 is made of a metallic material such as platinum, and iridium alloy. In another embodiment, conductor 456 is a metal wire other than the core of the guide wire. In another embodiment, PTVI device 410 is a guiding catheter such as a coronary guiding catheter. The coronary guiding catheter includes an elongate tubular body with a lumen extending between distal end portion 452 and proximal end portion 452. In another embodiment, PTVI device 410 includes two or more electrodes in distal end portion 451 and two or more conductors each connected between one of the electrodes and connector 458, which is a multi-conductor connector allowing for two or more electrically insulated connections.

Figure 5:
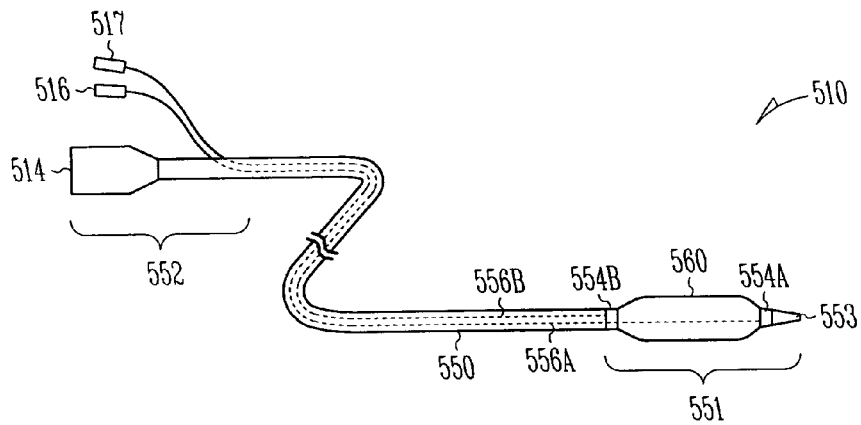
FIG. 5 is an illustration of another embodiment of a PTVI device with pacing electrodes.

FIG. 5 is an illustration of another embodiment of a PTVI device 510. PTVI device 510 is another specific embodiment of PTVI device 110 and has an elongate body 550 between a distal end portion 551 and a proximal end portion 552. Distal end portion 551 is configured for intravascular placement and includes a distal tip 553 and an angioplasty device 560. Angioplasty device 560 has one end approximately adjacent to distal tip 553 and another end coupled to elongate body 550. In various embodiments, angioplasty device 560 allows for application of an angioplastic therapy such as vascular dilatation, stent delivery, brachytherapy (radiotherapy), atherectomy, or embolic protection. In one embodiment, angioplasty device 560 includes an adjustable portion that has controllable expandability and contractibility. In one specific embodiment, angioplasty device 560 includes a balloon that is inflated and deflated through a passageway longitudinally extending within elongate body 550 and connected between the chamber of the balloon and a connector at proximal end portion 552. The balloon is inflatable using an air pump connected to that connector. In one embodiment, distal tip 553 is a tapered tip that facilitates the insertion of PTVI device 510 into a blood vessel. A pacing electrode 554A is approximately adjacent to one end of angioplasty device 560. Another pacing electrode 554B is approximately adjacent to the other end of angioplasty device 560. A conductor 556A extends longitudinally within elongate body 550 and is connected between pacing electrode 554A and a pacing connector 516, which is part of proximal end portion 552. A conductor 556B extends longitudinally within elongate body 550 and is connected between pacing electrode 554B and a pacing connector 517, which is also part of proximal end portion 552.

In an alternative embodiment, pacing connectors 516 and 517 are physically integrated into one multi-conductor connector. Proximal end portion 552 also includes a proximal end device 514. Proximal end device 514 represents a structure that accommodates all the mechanical connection and access requirements, which depend on the function of angioplasty device 560. In one embodiment, proximal end device 514 includes an integrated device as illustrated in FIG. 5. In another embodiment, proximal end device 514 branches out into multiple connectors and/or other devices.

In one embodiment, elongate body 550 is an elongate cylindrical shaft having a diameter in a range of approximately 1 mm to 5 mm. PTVI device 510 has a length in a range of approximately 50 cm to 150 cm. In one embodiment, angioplasty device 560 has a fixed, substantially cylindrical shape with a diameter in a range of approximately 1 mm to 10 mm. In another embodiment, angioplasty device 560 has an adjustable, substantially cylindrical or semi-spherical shape with a maximum diameter in a range of approximately 1 mm to 10 mm when fully expanded and a maximum diameter in a range of approximately 0.5 mm to 5 mm when fully contracted. In one embodiment, PTVI device 510 is a PTCA catheter and includes a lumen longitudinally extending within elongate body 550 to accommodate at least a portion of a guide wire such as PTVI device 410. In one embodiment, conductors 556A and 556B are each made of a metallic material such as stainless steel and alloys of nickel, titanium, and cobalt. Electrodes 554A and 554B are each made of a metallic material such as platinum, and iridium alloy. Elongate body 550 has a tubular outer shell made of a material such as silicone, polyurethane, Teflon, and polytetrafluoroethylene (PTFE).

In one alternative embodiment, PTVI device 510 includes one electrode in distal end portion 551 and one conductor connected between that electrode and a pacing connector in proximal end portion 552. In another alternative embodiment, PTVI device 510 includes three or more electrodes in distal end portion 551 and three or more conductors each connected between one of the electrodes a pacing connector in proximal end portion 552.

Figure 6:
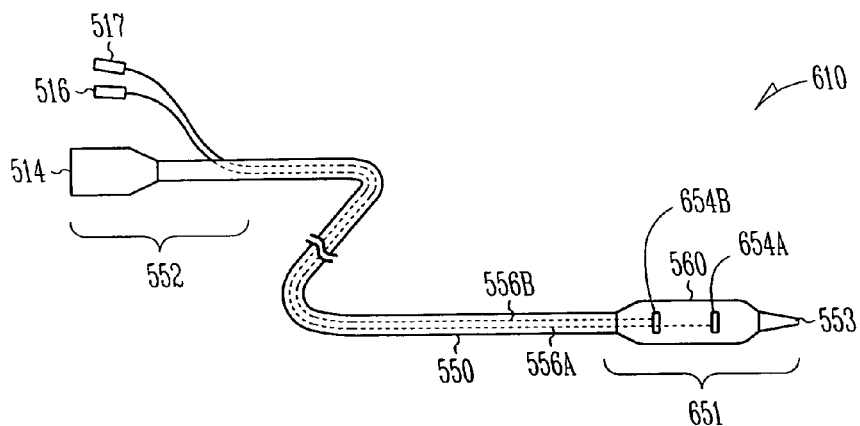
FIG. 6 is an illustration of another embodiment of a PTVI device with pacing electrodes.

FIG. 6 is an illustration of another embodiment of a PTVI device 610 with pacing electrodes. PTVI device 610 is another specific embodiment of PTVI device 110 and is similar to PTVI device 510 except for the location of the pacing electrodes. PTVI device 610 has a distal end portion 651, where pacing electrodes 654A and 654B are attached onto angioplasty device 560. In one specific embodiment, pacing electrodes 654A and 654B are each approximately adjacent to one end of angioplasty device 560.

PTVI devices 410, 510, and 610 are illustrated in FIGS. 4-6 for illustrative but not restrictive purposes. For example, the one or more pacing electrodes can be distributed on the distal portion of a PTVI device in any way allowing proper delivery of pacing pulses. In various embodiments, the one or more pacing electrodes can be distributed on the angioplasty device, the distal tip, and/or the elongate body at the distal end portion of the PTVI device.

FIGS. 7-13 illustrate exemplary specific embodiments of the distal end of a PTVI device with one or more pacing electrodes. In one embodiment, PTVI device 410, 510, and 610 are each made by modifying a selected product of Guidant Corporation's Vascular Intervention division ("Guidant VI," Temecula, Calif.) to include one or more pacing electrodes. Examples of such a selected product are illustrated in FIGS. 7-13. According to the present subject matter, one or more pacing electrodes are incorporated onto any PTVI device as deemed appropriate by one skilled in the art.

Such PTVI devices include, but are not limited to, devices that belong to the same category as those illustrated in FIGS. 7-13.

Figure 7:
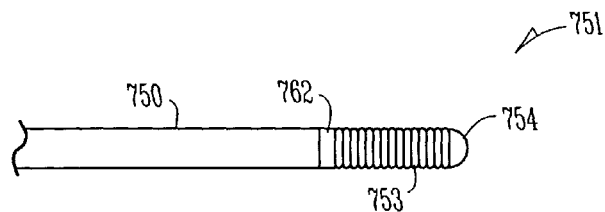
FIG. 7 is an illustration of an exemplary specific embodiment of the distal end portion of a PTVI device with pacing electrode(s).

FIG. 7 is an illustration of an embodiment of the distal end portion 751, which is an exemplary specific embodiment of distal end portion 451. Distal end portion 751 is the distal portion of a coronary guide wire (Guidant VI's HI-TORQUE PILOT™ 50 Guide Wire with Hydrocoat hydrophilic coating) modified to include a pacing electrode 754. The coronary guide wire includes an elongate body 750 being an insulated conductive wire that extends to a distal tip 753. The coronary guide wire has a length of approximately 190 cm or 300 cm, depending on the specific product model, and a diameter of approximately 0.014 inches (0.3556 mm). The conductive wire is connected to pacing electrode 754 at the distal end of distal tip 753. Distal end portion 751 also includes a radiopaque marker 762, which allows for measurement of legion length. In one embodiment, the single-electrode configuration allows the coronary guide wire to have a relatively small diameter. In one embodiment, pacing pulses are delivered using a unipolar electrode configuration, with a return electrode such as reference electrode 122.

Figure 8:
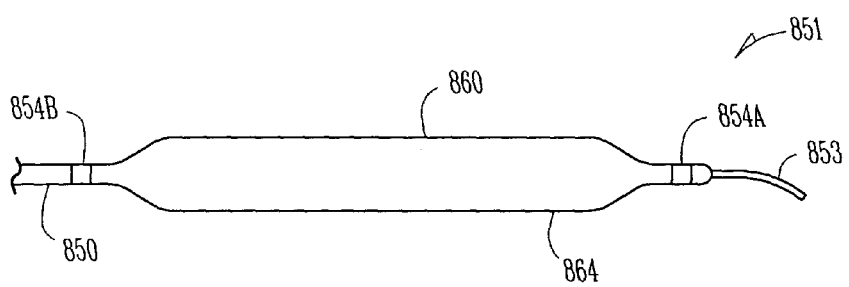
FIG. 8 is an illustration of another exemplary specific embodiment of the distal end portion of a PTVI device with pacing electrode(s).

FIG. 8 is an illustration of an embodiment of the distal end portion 851, which is an exemplary specific embodiment of distal end portion 551. Distal end portion 851 is the distal portion of a coronary dilatation balloon catheter (Guidant VI's VOYAGER™ RX Coronary Dilatation Catheter) modified to include pacing electrodes 854A and 854B. Distal end portion 851 is extended from an elongate body 850 and includes a tapered tip 853 and an angioplasty device 860. The coronary dilatation balloon catheter has a usable catheter working length of approximately 143 cm and accommodates a guide wire having a maximum diameter of 0.014 inches (0.3556 mm), such as the coronary guide wire illustrated in FIG. 7, that is used for insertion of the catheter. Elongate body 850 includes a shaft having a diameter in a range of approximately 2.0 to 2.8 French, depending on the specific product model. Angioplasty device 860 is a specific embodiment of angioplasty device 560 and includes an adjustable balloon 864 that is approximately adjacent to tapered tip 853. Adjustable balloon 864 is used for coronary dilatation by inflation. When inflated, adjustable balloon 864 has a diameter in a range of 1.5 mm to 4 mm, depending on the specific product model. Pacing electrode 854A is approximately adjacent to one end of adjustable balloon 864. Pacing electrode 854B is approximately adjacent to the other end of adjustable balloon 864. Pacing pulses are delivered using a bipolar configuration with pacing electrodes 854A and 854B, a unipolar configuration using one of pacing electrodes 854A and 854B and a return electrode such as reference electrode 122, or a combination of bipolar and unipolar configurations.

Figure 9:
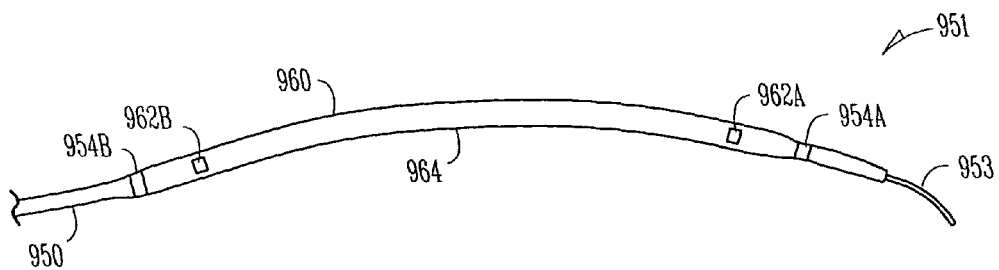
FIG. 9 is an illustration of another exemplary specific embodiment of the distal end portion of a PTVI device with pacing electrode(s).

FIG. 9 is an illustration of an embodiment of the distal end portion 951, which is an exemplary specific embodiment of distal end portion 551. Distal end portion 951 is the distal portion of a stent delivery platform (Guidant VI's GUIDANT MULTI-LINK RX ULTRA™ Coronary Stent System) modified to include pacing electrodes 954A and 954B. Distal end portion 951 is extended from an elongate body 950 and includes a tip 953 and an angioplasty device 960. The stent delivery platform accommodates a guide wire having a maximum diameter of 0.014 inches (0.3556 mm), such as the coronary guide wire illustrated in FIG. 7, that is used for insertion of the device. Angioplasty device 960 is a specific embodiment of angioplasty device 560 and includes an adjustable balloon 964 that is approximately adjacent to tip 953. Adjustable balloon 964 is used for placing a stent in the coronary artery where distal end portion 951 has reached. Depending on the specific product model, the working size of adjustable balloon 964 accommodates stents having a diameter in a range of approximately 3.5 mm to 5 mm and a length in a range of approximately 13 mm to 38 mm Pacing electrode 954A is approximately adjacent to one end of adjustable balloon 964. Pacing electrode 954B is approximately adjacent to the other end of adjustable balloon 964. Distal end portion 951 also includes a pair of radiopaque markers 962A and 962B on adjustable balloon 964 for indicating the balloon's working length. Pacing pulses are delivered using a bipolar configuration with pacing electrodes 954A and 954B, a unipolar configuration using one of pacing electrodes 954A and 954B and a return electrode such as reference electrode 122, or a combination of bipolar and unipolar configurations.

Figure 10:
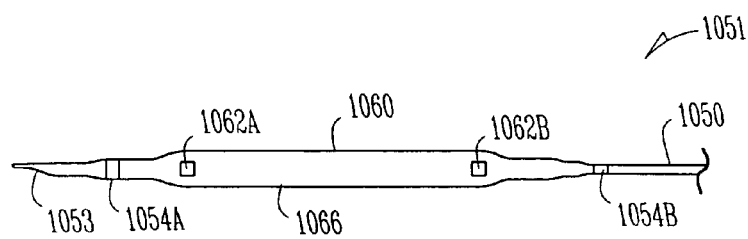
FIG. 10 is an illustration of another exemplary specific embodiment of the distal end portion of a PTVI device with pacing electrode(s).

FIG. 10 is an illustration of an embodiment of the distal end portion 1051, which is an exemplary specific embodiment of distal end portion 551. Distal end portion 1051 is the distal portion of a brachytherapy device (Guidant VI's GALILEO® Intravascular Radiotherapy System) modified to include pacing electrodes 1054A and 1054B. Distal end portion 1051 is extended from an elongate body 1050 and includes a tapered tip 1053 and an angioplasty device 1060. The brachytherapy device accommodates a guide wire having a maximum diameter of 0.014 inches (0.3556 mm), such as the coronary guide wire illustrated in FIG. 7, that is used for insertion of the device. Angioplasty device 1060 is a specific embodiment of angioplasty device 560 and includes an brachytherapy device 1066 that is approximately adjacent to tapered tip 1053 and includes a chamber containing an radiological agent to provide therapeutic doses to the tissue area where distal end portion 1051 has reached. Brachytherapy device 1066 has diameter in a range of approximately 2.5 mm, 3.0 mm, or 3.5 mm and a therapeutic dose length of approximately 32 mm or 52 mm, depending on the specific product model. Pacing electrode 1054A is approximately adjacent to one end of brachytherapy device 1066. Pacing electrode 1054B is approximately adjacent to the other end of brachytherapy device 1066. Distal end portion 1051 also includes a pair of radiopaque markers 1062A and 1062B on brachytherapy device 1066 for indicating the therapeutic dose length. Pacing pulses are delivered using a bipolar configuration with pacing electrodes 1054A and 1054B, a unipolar configuration using one of pacing electrodes 1054A and 1054B and a return electrode such as reference electrode 122, or a combination of bipolar and unipolar configurations.

Figure 11:
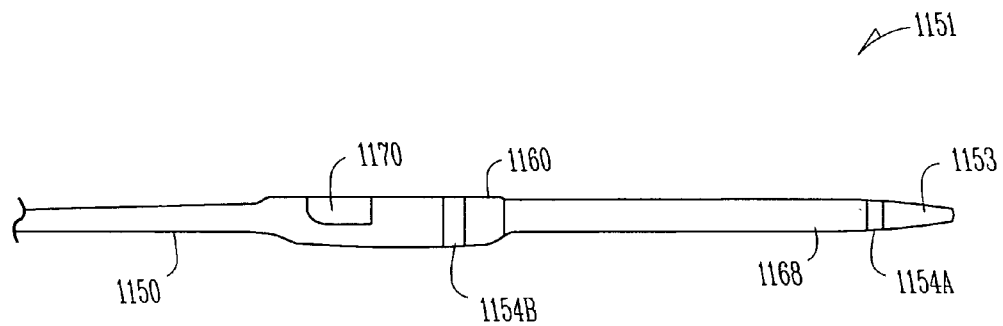
FIG. 11 is an illustration of another exemplary specific embodiment of the distal end portion of a PTVI device with pacing electrode(s).

FIG. 11 is an illustration of an embodiment of the distal end portion 1151, which is an exemplary specific embodiment of distal end portion 551. Distal end portion 1151 is the distal portion of an atherectomy device (Guidant VI's FLEXI-CUT® Directional Debulking System) modified to include pacing electrodes 1154A and 1154B. Distal end portion 1151 is extended from an elongate body 1150 and includes a tapered tip 1153 and an angioplasty device 1160. The atherectomy device has a working length of approximately 134 cm. Angioplasty device 1160, which is a specific embodiment of angioplasty device 560, is an atherectomy device that includes a cylindrical nosecone 1168 that is approximately adjacent to tapered tip 1153 and a cutter 1170 connected to cylindrical nosecone 1168. Cutter 1170 cuts the plaques that block or narrow the portion of the coronary artery where distal end portion 1151 has reached. Cylindrical nosecone 1168 stores the cut plaques. Depending on the specific product model, atherectomy device is capable of operating in blood vessels having diameters ranging from approximately 2.5 mm to 4 mm. Pacing electrode 1154A is on tapered tip 1153 and approximately adjacent to the distal end of cylindrical nosecone 1168. Pacing electrode 1154B is on cutter 1170 and approximately adjacent to the distal end of cutter 1170. Pacing pulses are delivered using a bipolar configuration with pacing electrodes 1154A and 1154B, a unipolar configuration using one of pacing electrodes 1154A and 1154B and a return electrode such as reference electrode 122, or a combination of bipolar and unipolar configurations.

Figure 12:
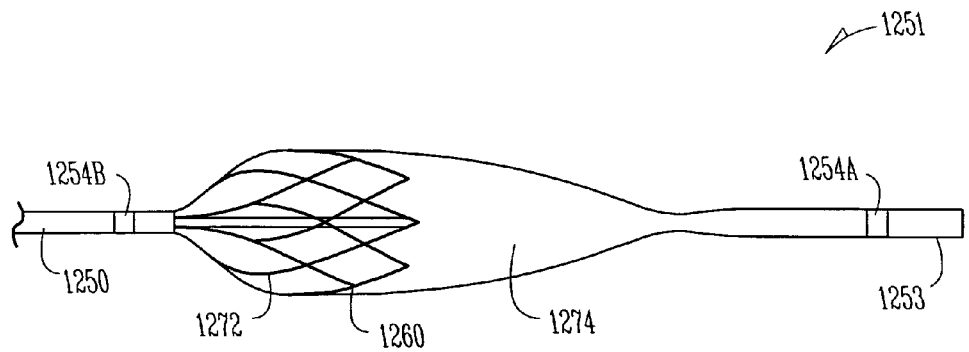
FIG. 12 is an illustration of another exemplary specific embodiment of the distal end portion of a PTVI device with pacing electrode(s).

FIG. 12 is an illustration of an embodiment of the distal end portion 1251, which is an exemplary specific embodiment of distal end portion 551. Distal end portion 751 is the distal portion of a distal embolization protection device (Guidant VI's RX ACCUNETT™ Embolic Protection System) modified to include pacing electrodes 1254A and 1254B. Distal end portion 1251 is extended from an elongate body 1250 and includes a tip 1253 and an angioplasty device 1260. Elongate body 1250 is based on a coronary guide wire that has a diameter of 0.014 inches (0.3556 mm) and extends throughout substantially the full length of the distal embolization protection device, which is either 190 cm or 300 cm, depending on the specific product model. Angioplasty device 1260, which is a specific embodiment of angioplasty device 560, is an embolic protection device that includes a filter basket 1272 with a filter membrane 1274 to contain and remove embolic material including plaques dislodged during the angioplastic procedure. Filter basket 1272 is flexible, with available basket diameters (when fully expanded) of 4.5 mm, 5.5 mm, 6.5 mm, and 7.5 mm, depending on the specific product model. Pacing electrode 1254A is on tip 1253. Pacing electrode 1254B is on elongate body 1250 and is approximately adjacent to the proximal end of filter basket 1272. Pacing pulses are delivered using a bipolar configuration with pacing electrodes 1254A and 1254B, a unipolar configuration using one of pacing electrodes 1254A and 1254B and a return electrode such as reference electrode 122, or a combination of bipolar and unipolar configurations.

Figure 13:
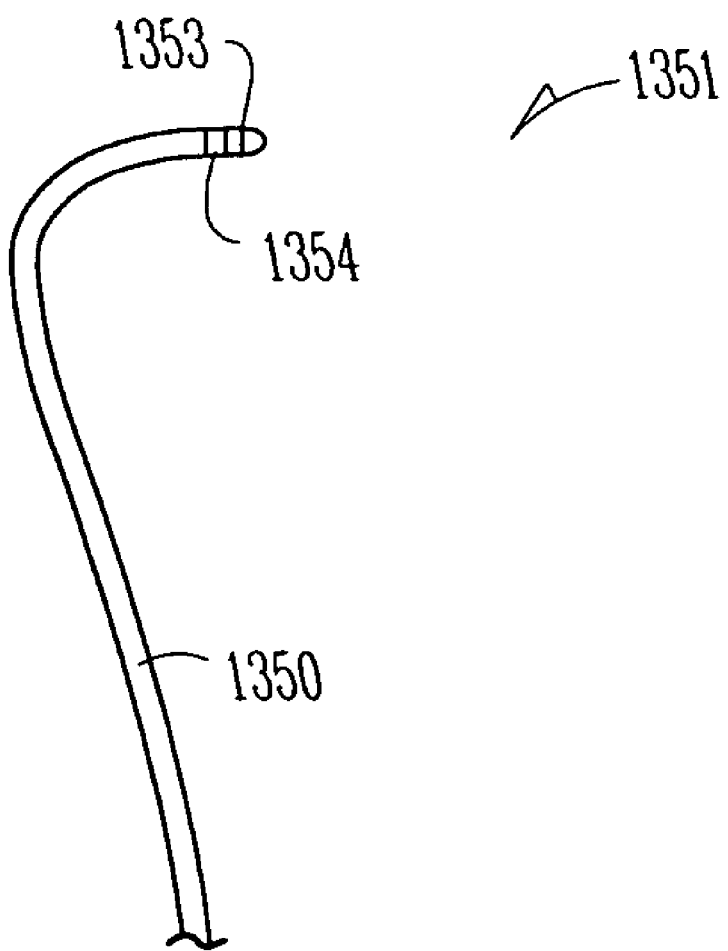
FIG. 13 is an illustration of another exemplary specific embodiment of the distal end portion of a PTVI device with pacing electrode(s).

FIG. 13 is an illustration of an embodiment of the distal end portion 1351, which is another exemplary specific embodiment of distal end portion 451. Distal end portion 1351 is the distal portion of a coronary guiding catheter (Guidant VI's VIKING OPTIMA™ 50 Guiding Catheter) modified to include a pacing electrode 1354. The coronary guiding catheter includes a tubular elongate body 1350 that has a distal tip 1353, and a lumen having a diameter of 6 French (0.068 inches), 7 French (0.078 inches), or 8 French (0.091 inches). In one embodiment, the single-electrode configuration allows the coronary guiding catheter to have a relatively small diameter. In one embodiment, pacing pulses are delivering using a unipolar electrode configuration, with a return electrode such as reference electrode 122.

It is to be understood that the above detailed description, including the various configurations of PTVI devices, is intended to be illustrative, and not restrictive. In general, cardiac protection pacing is applied to prevent or reduce cardiac injury and/or occurrences of arrhythmia caused by an ischemic event by using one or more pacing electrodes incorporated onto any intravascular device and a pacemaker that is capable of delivering pacing pulses according to a predetermined cardiac protection pacing sequence. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for use during revascularization of a coronary artery, comprising:
   a pacemaker including;
      a pacing output circuit; and
      a control circuit coupled to the pacing output circuit, the control circuit including a cardiac protection pacing sequence timer configured to time a predetermined cardiac protection pacing sequence configured to prevent cardiac injury caused by occlusion of the coronary artery during the revascularization, the cardiac protection pacing sequence including alternating pacing and non-pacing periods, the pacing periods each having a predetermined pacing duration during which a plurality of pacing pulses are delivered from the pacing output circuit in a predetermined pacing mode, the non-pacing periods each having a predetermined non-pacing duration during which no pacing pulse is delivered; and
   a percutaneous transluminal vascular intervention device including:
      a proximal end portion including one or more pacing connectors configured to be connected to the pacing output circuit;
      a distal end portion configured for intravascular placement, the distal end portion including a distal tip;
      an elongate body coupled between the proximal end portion and the distal tip;
      one or more pacing electrodes incorporated onto the distal end portion; and
      one or more conductors each coupled between one of the one or more pacing electrodes and one of the one or more pacing connectors,
      wherein the percutaneous transluminal vascular intervention device is coupled to the pacemaker to allow the plurality of pacing pulses to be delivered from the pacing output circuit to the one or more pacing electrodes through the one or more pacing connectors.

2. The system of claim 1, wherein the percutaneous transluminal vascular intervention device comprises one of a coronary guide wire and a coronary guiding catheter.

3. The system of claim 2, wherein the elongate body comprises an elongate cylindrical shaft having a diameter in a range of approximately 0.2 mm to 1.5 mm.

4. The system of claim 2, wherein the elongate body comprises an elongate tubular body having an outer diameter in a range of approximately 0.5 mm to 8 mm and an inner diameter in a range of approximately 0.4 mm to 7 mm.

5. The system of claim 1, wherein the distal end portion comprises an angioplasty device having a first end approximately adjacent to the distal tip and a second end coupled to the elongate body.

6. The system of claim 5, wherein the one or more pacing electrodes comprises a first electrode approximately adjacent to the first end of the angioplasty device.

7. The system of claim 6, wherein the one or more pacing electrodes further comprises a second electrode approximately adjacent to the second end of the angioplasty device.

8. The system of claim 6, wherein the angioplasty device comprises an adjustable angioplasty device having controllable expandability and contractibility.

9. The system of claim 6, wherein the percutaneous transluminal vascular intervention device comprises one of a coronary dilatation balloon catheter, a stent delivery platform, a brachytherapy device, an atherectomy device, and an embolization protection device.

10. The system of claim 5, wherein the elongate body comprises an elongate cylindrical shaft having a diameter in a range of approximately 1 mm to 5 mm.

11. The system of claim 5, wherein the one or more pacing electrodes comprises at least one pacing electrode incorporated onto the distal tip.

12. The system of claim 5, wherein the one or more pacing electrodes comprises at least one pacing electrode incorporated onto the angioplasty device.

13. The system of claim 5, wherein the one or more pacing electrodes comprises at least one pacing electrode incorporated onto the elongate body.

14. The system of claim 5, wherein the angioplasty device comprises an adjustable angioplasty device having controlled expandability and contractibility.

15. The system of claim 14, wherein the adjustable angioplasty device comprises an adjustable balloon.

16. The system of claim 15, wherein the adjustable balloon comprises a coronary dilatation balloon configured for coronary dilatation.

17. The system of claim 15, wherein the adjustable balloon comprises a coronary stent delivery balloon adapted for coronary stent placement.

18. The system of claim 5, wherein the angioplasty device comprises a distal embolization protection device including an adjustable filter basket adapted to contain and remove embolic material.

19. The system of claim 5, wherein the angioplasty device comprises a brachytherapy device including a chamber containing a radiological agent.

20. The system of claim 5, wherein the angioplasty device comprises an atherectomy device including a cylindrical nosecone coupled to the distal tip and a cutter to the nosecone, the cutter adapted to cut tissue, the cylindrical nosecone adapted to store cut tissue.

21. The system of claim 1, wherein the predetermined pacing duration is in a range of approximately 10 seconds to 20 minutes, and the predetermined non-pacing duration is in a range of approximately 10 seconds to 20 minutes.

* * * * *

UNITED STATES PATENT AND TRADEMARK OFFICE
CERTIFICATE OF CORRECTION

| | | |
|---|---|---|
| PATENT NO. | : 7,962,208 B2 | Page 1 of 1 |
| APPLICATION NO. | : 11/113828 | |
| DATED | : June 14, 2011 | |
| INVENTOR(S) | : Allan C. Shuros et al. | |

It is certified that error appears in the above-identified patent and that said Letters Patent is hereby corrected as shown below:

In column 11, line 15, delete "ACCUNETT™" and insert -- ACCUNET™ --, therefor.

Signed and Sealed this
Thirtieth Day of August, 2011

David J. Kappos
*Director of the United States Patent and Trademark Office*